United States Patent [19]

Lempert et al.

[11] Patent Number: 5,240,918

[45] Date of Patent: Aug. 31, 1993

[54] 2-(SUBSTITUTED IMINO)-THIAZOLIDINES AND PROCESS FOR THE PREPARATION THEREOF

[75] Inventors: Károly Lempert; Gyula Hornyák; József Fetter; Antal Feller; Klára Gasó; Gábor Gigler; László Kápolnai; Lujza Petócaz; Katalin Szemerédi; Márton Fekete, all of Budapest, Hungary

[73] Assignee: EGIS Gyogyszergyar, Budapest, Hungary

[21] Appl. No.: 857,067

[22] Filed: Mar. 24, 1992

[51] Int. Cl.⁵ ................ C07D 277/18; A61K 31/425
[52] U.S. Cl. .................................... 514/370; 514/371; 548/195; 548/196
[58] Field of Search ............... 548/195, 196; 514/370, 514/371

[56] References Cited

U.S. PATENT DOCUMENTS 4,616,025 10/1986 Ezer ................................... 514/342
4,867,780 9/1989 Woolard ............................... 71/90

Primary Examiner—Robert Gerstl
Attorney, Agent, or Firm—Beveridge, DeGrandi, Weilacher & Young

[57] ABSTRACT

The invention relates to new 2-(substituted imino)-thiazolidines, a process for the preparation thereof, pharmaceutical compositions comprising the same, the use of the said 2-(substituted imino)thiazolidines for the treatment of diseases and for the preparation of pharmaceutical compositions suitable for the treatment of diseases.

The new 2-(substituted imino)-thiazolidine derivatives provided by the present invention correspond to the general formula (I),

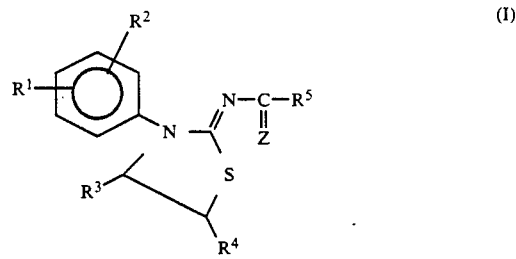

wherein
$R^1$ and $R^2$ each represent halogen, nitro, $C_{1-4}$ alkoxy or $C_{1-4}$ alkyl, which latter may optionally carry one or more halogen substituent(s),
$R^3$ and $R^4$ each represent hydrogen or $C_{1-4}$ alkyl,
Z denotes oxygen, sulfur or imino, which latter is substituted by a $C_{1-6}$ alkyl or a $C_{1-6}$ alkenyl group,
$R^5$ stands for hydrogen, $C_{1-4}$ alkyl, $C_{1-4}$ alkylthio or a group or the formula —NH—R, wherein R represents $C_{1-6}$ alkyl, aryl, aralkyl or $C_{1-6}$ alkenyl optionally carrying a halogen or a di-($C_{1-4}$ alkyl)-amino substituent; or
Z and $R^5$ together stand for a trivalent nitrogen atom, with the proviso that if Z denotes a substituted imino group, $R^5$ stands for $C_{1-4}$ alkylthio, and if $R^5$ is $C_{1-4}$ alkylthio, Z represents a substituted imino, and with the further proviso that if Z denotes sulfur, $R^5$ is other than hydrogen or $C_{1-4}$ alkyl, and possess valuable antianginal and analgesic properties.

2 Claims, No Drawings

2-(SUBSTITUTED IMINO)-THIAZOLIDINES AND PROCESS FOR THE PREPARATION THEREOF

This invention relates to new 2-(substituted imino)-thiazolidine derivatives, a process for the preparation thereof, pharmaceutical compositions comprising the same, to the use of the said 2-(substituted imino)-thiazolidine derivatives for the treatment of diseases and for the preparation of pharmaceutical compositions suitable for the treatment of diseases.

According to an aspect of the present invention there are provided new 2-(substituted imino)-thiazolidine derivatives of the general formula (I),

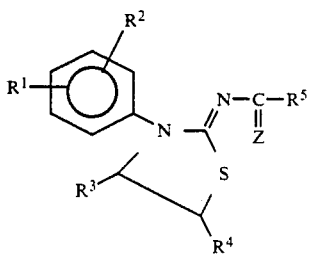

wherein
$R^1$ and $R^2$ each represent halogen, nitro, $C_{1-4}$ alkoxy or $C_{1-4}$ alkyl, which latter may optionally carry one or more halogen substituent(s),
$R^3$ and $R^4$ each represent hydrogen or $C_{1-4}$ alkyl,
Z denotes oxygen, sulfur or imino, which latter is substituted by a $C_{1-6}$ alkyl or a $C_{1-6}$ alkenyl group,
$R^5$ stands for hydrogen, $C_{1-4}$ alkyl, $C_{1-4}$ alkylthio or a group or the formula —NH—R wherein R represents $C_{1-6}$ alkyl, aryl, aralkyl or $C_{1-6}$ alkenyl optionally carrying a halogen or a di-($C_{1-4}$ alkyl)-amino substituent; or
Z and $R^5$ together stand for a trivalent nitrogen atom, with the proviso that if Z denotes a substituted imino group, $R^5$ stands for $C_{1-4}$ alkylthio, and if $R^5$ is $C_{1-4}$ alkylthio, Z represents a substituted imino, and with the further proviso that if Z denotes sulfur, $R^5$ is other than hydrogen or $C_{1-4}$ alkyl,
and pharmaceutically acceptable salts thereof.

The compounds according to the present invention possess valuable antianginal and analgesic effects.

The term "alkyl group" used throughout the specification relates to straight or branched chained saturated aliphatic hydrocarbon groups having 1 to 4 carbon atom(s), e.g. methyl, ethyl, propyl, isopropyl, n-butyl, tert. butyl etc. The term "alkoxy group" relates to alkyl ether groups comprising $C_{1-4}$ carbon atoms, e.g. methoxy, ethoxy, tert. butoxy etc. As "$C_{2-6}$ alkenyl groups" straight or branched chained alkenyl groups are mentioned, e.g. vinyl, allyl, 2-methylallyl, 1-propenyl, 1-butenyl, 2-butenyl, 2-hexenyl etc. The "di($C_{1-4}$ alkyl)-amino groups" comprise alkyl groups containing the given number of carbon atom(s) (e.g. dimethylamino, diethylamino, diisopropylamino etc). The term "halogen atom" encompasses all the four halogen atoms (fluorine, chlorine, bromine and iodine). The term "alkylthio group" covers e.g. the methylthio, ethylthio, n-propylthio groups. The term "aryl group" relates to aromatic groups such as phenyl or naphthyl. As "aralkyl groups" alkyl groups carrying a phenyl or naphthyl substituent are mentioned, e.g. benzyl or β-phenylethyl.

The compounds of the general formula (I), wherein $R^5$ stands for $C_{1-4}$ alkylthio or a group of the formula —NH—R—, wherein R represents $C_{1-6}$ alkyl, aryl, aralkyl or $C_{1-6}$ alkenyl substituted by a di($C_{1-4}$ alkyl)-amino group, furthermore the compounds of the general formula (I), wherein Z and $R^5$ together stand for a trivalent nitrogen atom, when reacted with acids can form acid-addition salts. The pharmaceutically acceptable acid-addition salts of the compounds of the general formula (I) can be formed with inorganic or organic acids. As examples for the pharmaceutically acceptable acid-addition salts the chlorides, bromides, ethanesulfonates, tartarates, maleates and citrates can be mentioned.

Preferred representatives of the compounds of the general formula (I) are the following derivatives:
2-(N'-allylthiocarbamoylimino)-3-(5'-chloro-2'-nitrophenyl)-thiazolidine,
2-cyanimido-3-(5'-chloro-2'-nitrophenyl)thiazolidine,
2-acetylimino-3-(4'-chloro-2'-nitrophenyl)thiazolidine,
and pharmaceutically acceptable salts thereof.

According to a further aspect of the present invention there is provided a process for the preparation of 2-(substituted imino)-thiazolidine derivatives of the general formula (I) and pharmaceutically acceptable acid-addition salts thereof, which comprises
a) for the preparation of compounds of the general formula (I), wherein Z stands for oxygen and $R^5$ represents hydrogen or $C_{1-4}$ alkyl, reacting a 2-iminothiazolidine of the general formula (II),

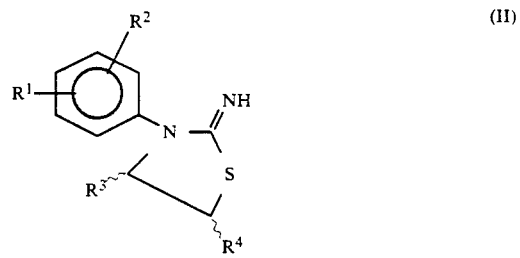

wherein $R^1$, $R^2$, $R^3$ and $R^4$ are as stated above, with an acylating agent of the general formula (III),

wherein X stand for halogen or acyloxy, Z represents oxygen and $R^5$ denotes hydrogen or $C_{1-4}$ alkyl, with the proviso that if X stands for halogen, $R^5$ is $C_{1-4}$ alkyl; or
b) for the preparation of compounds of the general formula (I), wherein Z stands for oxygen or sulfur and $R^5$ is a group of the formula —NH—R, wherein R is as stated above, reacting a 2-iminothiazolidine of the general formula (II), wherein $R^1$, $R^2$, $R^3$ and $R^4$ are as stated above, with an isocyanate orisothiocyanate of the general formula (IV), $$Z=C=N-R \qquad (IV)$$

·wherein Z stands for oxygen or sulfur, and R is as stated above; or c) for the preparation of compounds of the general formula (I), wherein Z represents a substituted imino group and $R^5$ is $C_{1-4}$ alkylthio, reacting a compound of the general formula (I), wherein Z stands for sulfur and $R^5$ represents a group of the general formula —NH—R, wherein R is $C_{1-6}$ alkyl or $C_{1-6}$ alkenyl, with an alkyl halide of the general formula (V),

Alk—X     (V)

wherein Alk represents $C_{1-4}$ alkyl and X stands for halogen; or d) for the preparation of compounds of the general formula (I), wherein Z and $R^5$ together represent a trivalent nitrogen atom, reacting a 2-iminothiazolidine of the general formula (II), wherein $R^1$, $R^2$, $R^3$ and $R^4$ are as stated above, with a cyanohalide of the general formula (VI),

X—C≡N     (VI)

wherein X stands for halogen;
and, if possible and desired, converting a compound of the general formula (I) thus obtained into a pharmaceutically acceptable acid-addition salt thereof, or setting free a base of the general formula (I) from a salt thereof, or converting an acid-addition salt of a base of the general formula (I) into another acid-addition salt thereof.

According to variant a) of the process according to the invention compounds of the general formula (I), wherein Z stands for oxygen and $R^5$ represents hydrogen or $C_{1-4}$ alkyl, are prepared by acylating a 2-iminothiazolidine of the general formula (II). As acylating agent a carboxylic halide, carboxylic anhydride or mixed anhydride (e.g. acetyl chloride, acetic anhydride or the mixed anhydride of acetic acid and formic acid) may be used. If a carboxylic halide is used as acylating agent, the reaction is carried out in the presence of an acid-binding agent. For this purpose preferably triethylamine or pyridine can be used. The acylation is preferably performed in a protic or aprotic solvent, such as chloroform or acetic acid, at an elevated temperature, preferably at the boiling point of the solvent. The reaction time is generally 0.5–2 hour(s). The product thus obtained is isolated from the reaction mixture by methods known per se. e.g. evaporation and crystallization from an appropriate solvent.

According to variant b) of the process according to the invention compounds of the general formula (I), wherein Z represents oxygen or sulfur and $R^5$ denotes a substituted amino group, are prepared by reacting a compound of the general formula (II) with an isocyanate or isothiocyanate of the general formula (IV). The reaction is preferably carried out in a dipolar aprotic solvent, preferably acetonitrile, at an elevated temperature. It is preferable to perform the reaction at the boiling point of the solvent. The reaction time is generally 2–10 hours. The compound of the general formula (I) obtained in the reaction is isolated either as a base or as an acid-addition salt after distilling off the solvent, in the form of crystals.

According to variant c) of the process according to the invention compounds of the general formula (I), wherein Z represents a substituted imino group and $R^5$ stands for $C_{1-4}$ alkylthio, are prepared. As starting substance a compound of the general formula (I), wherein Z is sulfur and $R^5$ represents a substituted amino carrying a $C_{1-6}$ alkyl or $C_{1-6}$ alkenyl substituent, is used which can be produced according to process variant b). Said starting substance is S-alkylated with an alkyl halide. The reaction is preferably carried out in a protic solvent, preferably in a lower alcohol, at an elevated temperature, preferably at the boiling point of the reaction mixture. The product thus obtained is separated from the reaction mixture by evaporation or by the addition of a solvent (such as ether).

According to process variant d) compounds of the general formula (I), wherein Z and $R^5$ together represent a trivalent nitrogen atom, are produced. For this purpose a 2-iminothiazolidine of the general formula (II) is reacted with a cyanohalide of the general formula (VI), preferably with bromine cyan. The reaction is preferably carried out in a dipolar aprotic solvent, preferably acetonitrile, at an elevated temperature, preferably at the boiling point of the solvent. The reaction time is generally 3 to 5 hours. The product thus obtained is crystallized from the reaction mixture either in the form of a free base or in the form of an acid-addition salt by cooling or by adding a solvent such as ether to it.

The compounds of the general formula (I), wherein $R^5$ stands for $C_{1-4}$ alkylthio or a group of the formula —NH—R, wherein R represents $C_{1-6}$ alkyl, aryl, aralkyl or $C_{1-6}$ alkenyl substituted by a di($C_{1-4}$ alkyl)-amino group, furthermore the compounds of the general formula (I), wherein Z and $R^5$ together stand for a trivalent nitrogen atom, can be reacted with organic or inorganic acids to form acid-addition salts. On the other hand, the free bases of the general formula (I) may be liberated from the acid-addition salts thereof, and the acid-addition salts may be converted into other acid-addition salts. These reactions can be performed by methods known per se.

The compounds of the general formula (II) used as starting substances are known, the process for their preparation is provided in Hungarian patent specification No. 191,408. The compounds of the general formulae (III), (IV), (V) and (VI) are commercial products or can be prepared by methods known per se.

The compounds according to the present invention exhibit excellent biological activity, they possess antianginal and analgesic properties.

The activity of the compounds of the invention has been examined by the following tests.

1. Antianginal effect

Method: the test was carried out on rats by using the method of Nieschulz, E., Popendiker, K. and Hoffmann, I. (Arzneimittel Forschung, 5, 680 /1955/).

Male rats of 180–220 g body weight were narcotized with chloralese-urethane (70–700 mg/kg ip.). The ECG was registered with needle electrodes in standard II leading. The experimental coronaria insufficiency was induced with vasopressin NE/kg i.v.). The height of wave T in ECG was measured before and after the administration of vasopressin in both the control and treated groups. Test compounds were administered intravenously 2 minutes prior to the treatment with vasopressin. The results are summarized in Table I.

TABLE I

| Test compound (Example No.) | Antianginal effect Activity (2 mg/kg iv.) | $ED_{50}$ mg/kg (iv.) |
|---|---|---|
| 46 | 62% | 1.76 |
| 20 | 78% | 1.45 |
| Prenylamine | 32% | 6.5 |

As the above data show, the most effective compounds of the present invention exhibit an antianginal effect which is considerably higher than that of Prenylamine.

2. Acetic acid "writhing test" on mice (analgesic effect)

Method: Newbould, Brit. J. Pharmacol., 35, 487 (1969)

The test is carried out according to the method of Newbould on white mice except that the amount of intraperitoneally administered acetic acid is modified. More reliable responses are obtained by using a concentration of 0.75%, a dose of 20 mg/kg and a volume of 20 ml/kg. In the period between the 5th and 10th minutes following the administration of acetic acid the number of the characteristic "writhing" responses is counted for each animal and the "total writhing number" (within 5 minutes) is expressed as the percentage of the value obtained for the control animals. The mice are treated with the test compound and the carrier, respectively, orally 1 hour before the administration of acetic acid. 12 animals are used per dose. The results are disclosed in Table II.

TABLE II

Acetic acid "writhing test" on mice

| Test compound No. of Example | $LD_{50}$ mg/kg | $ID_{50}$ mg/kg | Therapeutical index |
| --- | --- | --- | --- |
| 26 | 2000 | 170 | 11.8 |
| 25 | 2000 | 180 | 11.1 |
| 24 | 700 | 37 | 10.9 |
| Acetylsalicylic acid | 1350 | 260.8 | 5.2 |
| Phenyllanthasone | 1000 | 100–200 | 5–10 |

As the above data show, the toxicity values of the most effective compounds are much more favourable than those of the comparative substances used in the therapy.

According to a further aspect of the present invention there are provided pharmaceutical compositions comprising as active ingredient at least one compound of the general formula (I) or a pharmaceutically acceptable acid-addition salt thereof in admixture with suitable inert solid or liquid pharmaceutical carriers.

The pharmaceutical compositions of the present invention can be prepared by methods known per se by admixing the active ingredient with suitable inert solid or liquid carriers and bringing the mixture to galenic form.

The pharmaceutical compositions of the present invention may be suitable for oral (e.g. tablet, pill, coated pill, dragée, solid or soft gelatine capsule, solution, emulsion or suspension), parenteral (e.g. injection solution) or rectal (e.g. suppository) administration.

As carrier for the preparation of tablets, coated tablets, dragées and solid gelatine capsules e.g. lactose, corn starch, potatoe starch, talc, magnesium carbonate, magnesium stearate, calcium carbonate, stearic acid or the salts thereof, etc. can be used. As carrier for the soft gelatine capsules e.g. vegetable oils, fats, waxes or polyols of suitable consistency can be used. As carriers for the solutions and syrups e.g. water, polyols (polyethylene glycol), saccharose or glucose can be used. The injection solutions can comprise e.g. water, alcohols, polyols, glycerol or vegetable oils as carrier. The suppositories can be prepared with the aid of e.g. oils, waxes, fats or polyols of suitable consistency.

In addition the pharmaceutical formulations may comprise auxiliaries usually applied in the pharmaceutical industry, e.g. wetting, sweetening agents, aroma substances, salts causing the change of osmotic pressure, buffers, etc. The pharmaceutical formulations may further comprise other active ingredients, too.

The compounds of the general formula (I) can preferably be used in therapy orally in the form of tablets or capsules. Especially preferred are the capsules or tablets comprising about 50 mg of active ingredient.

The daily dose of the compounds of the general formula (I) can vary within wide ranges depending on several factors, e.g. on the activity of the active ingredient, the patient's condition and age, the severity of the disease, etc. The oral dose is generally 10 to 1000 mg/day, preferably 50 to 500 mg/day. It has to be stressed that these dose values are only of informative character and the administered dose must always be determined by the physician therapeutist.

According to a further aspect of the present invention there is provided the use of the compounds of the general formula (I) or pharmaceutically acceptable salts thereof for the preparation of pharmaceutical compositions having particularly antianginal and/or analgesic effects.

According to a still further aspect of the present invention there is provided a method of antianginal and/or analgesic treatment, which comprises administering to the patient an effective amount of a compound of the general formula (I) or a pharmaceutically acceptable salt thereof.

The invention is further illustrated by the following Examples of non-limiting character.

EXAMPLE 1

2-(N-Butylthiocarbamoylimino)-3-(5'-chloro-2'-nitrophenyl)-thiazolidine 1.3 g (5 mmoles) of 2-imino-3-(5'-chloro-2'-nitrophenyl)-thiazolidine and 2.1 g (10 mmoles) of butyl isothiocyanate are boiled in 20 ml of acetonitrile for 4 hours. Then the solution is clarified and evaporated in vacuo. The residual oil is crystallized from methanol.

Yield: 1.1 g (59%) of yellowish white crystals
M p.: 150–151° C. (MeOH)
TLC: Cyclohexane/ethyl acetate=1/2 $R_f$=0.6
Analysis for the formula $C_{14}H_{17}ClN_4S_2O_2$ (372.9)
Calculated: Cl=9.52%, S=17 19%,
Found: Cl=9.38%, S=17.13%,
IR (KBr): $\nu$NH 3380, $NO_2$ 1530, 1360/cm

EXAMPLE 2

3-(4'-Bromo-2'-nitrophenyl)-2-(N-propylcarbamoylimino)-thiazolidine 1 g (3 mmoles) of 3-(4'-bromo-2'-nitrophenyl)-2-iminothiazolidine and 0.52 g (6 mmoles) of propyl isocyanate are boiled in 30 ml of acetonitrile for 3 hours. The solution is then clarified and evaporated in vacuo. The crystalline residue is recrystallized from a mixture of ethyl acetate and hexane.

Yield: 0.8 g (68.9%) of yellowish green crystals
M.p.: 136–138° C. (EtOAc-hexane)
TLC: Chloroform/acetone=25/4 $R_f$=0.5
Analysis for the formula $C_{13}H_{15}BrN_4O_3S$ (387.3)
Calculated: Br=20.64%, S=8.28%,
Found: Br=20.58%, S=8.25%.
IR (KBr): $\nu$NH 3430, amide-I 1630, $NO_2$ 1350/cm

EXAMPLE 3

2-(N-Allylthiocarbamoylimino)-3-(4'-bromo-2'-nitrophenyl)-thiazolidine 0.6 g (2 mmoles) of 3-(4'-bromo-2'-nitrophenyl)-2-iminothiazolidine and 0.3 g (3 mmoles) of allyl isothiocyanate are boiled in 20 ml of acetonitrile for 6 hours. The solution is then clarified and evaporated in vacuo. The residual yellow oil is crystallized from methanol.

Yield: 0.6 g (74.6%) of yellowish white crystalline powder

M.p.: 115–116° C. (MeOH)

TLC: Cyclohexane/ethyl acetate=1/2 $R_f$=0.5

Analysis for the formula $C_{13}H_{13}BrN_4O_2S_2$(401.3)

Calculated: Br=19.91%, S=15.98%,

Found: Br=19.98%, S=15.94%.

IR (KBr): $\nu$NH 3365, $NO_2$ 1520, 1340/cm

EXAMPLE 4

2-(N-Methylthiocarbamoylimino)-3-(5'-chloro-2'-nitrophenyl)-thiazolidine 2.1 g (8 mmoles) of 2-imino-3-(5'-chloro-2'-nitrophenyl)-thiazolidine and 1.1 g (12 mmoles) of ethyl isothiocyanate are boiled in 20 ml of acetonitrile for 6 hours. The solution is then clarified and evaporated in vacuo and the crystalline residue is recrystallized from ethanol.

Yield: 1.8 g (65.2%) of yellowish white crystalline powder

M.p.: 163–165° C. (EtOH)

TLC: Cyclohexane/ethyl acetate=3/2 $R_f$=0.5

Analysis for the formula $C_{12}H_{13}ClN_4O_2S_2$ (344.8)

Calculated: Cl=10.29%, S=18.59%,

Found: Cl=10.37%, S=18.54%.

IR (KBr): $\nu$NH 3395, $NO_2$ 1540, 1330/cm

EXAMPLE 5

2-[(N-Benzylthiocarbamoyl)-imino]-3-(4-chloro-2-nitrophenyl)-thiazolidine 1.3 g (5 mmoles) of 2-imino-3-(4-chloro-2-nitrophenyl)-thiazolidine and 1 8 g (13 mmoles) of benzyl isothiocyanate are boiled in 30 ml of acetonitrile for 3 hours. The solution is then clarified and evaporated in vacuo. The residual yellow oil is crystallized from methanol.

Yield: 1.1 g (54%) of yellow needle crystals

M.p.: 179–180° C. (MeOH)

TLC: Chloroform/ethyl acetate=3/2 $R_f$=0.8

Analysis for the formula $C_{17}H_{15}ClN_4O_2S_2$ (406.9)

Calculated: Cl=8.72%, N=13.77%, S=15.76%,

Found: Cl=8.71%, N=13.92%, S=15.85%.

IR (KBr): $\nu$NH 3230, $NO_2$ 1515, 1340/cm

EXAMPLE 6

2-(N-Benzylthiocarbamoylimino)-3-(5'-chloro-2'-nitrophenyl)-thiazolidine 1.3 g (5 mmoles) of 2-imino-3-(5'-chloro-2'-nitrophenyl)-thiazolidine and 1.8 g (7 mmoles) of benzyl isothiocyanate are boiled in 30 ml of acetonitrile for 4 hours. The solution is then clarified and evaporated in vacuo. The crystalline residue is recrystallized from methanol.

Yield: 1.7 g (84%) of yellow crystalline powder

M.p.: 175° C. (MeOH)

TLC: Cyclohexane/ethyl acetate=3/2 $R_f$=0.6

Analysis for the formula $C_{17}H_{15}ClN_4O_2S_2$ (406.9)

Calculated: Cl=8.72%, S=15.76%,

Found: Cl=8.72%, S=15.86%.

IR (KBr): $\nu$NH 3250, $NO_2$ 1530, 1350/cm

EXAMPLE 7

2-(N-Butylcarbamoylimino)-3-(4'-chloro-2'-nitrophenyl)-thiazolidine 1.3 g (5 mmoles) of 2-imino-3-(4'-chloro-2'-nitrophenyl)-thiazolidine and 2.0 g (10 mmoles) of butyl isocyanate are boiled in 20 ml of acetonitrile for 6 hours. The solution is then clarified and evaporated in vacuo. The residual yellow oil is dissolved in ethyl acetate, the solution is clarified and evaporated again and the residue is crystallized from hexane.

Yield: 1.05 g (59%) of yellowish white crystalline powder

M.p.: 73–74° C. (EtOAc-hexane)

TLC: Cyclohexane/ethyl acetate=1/2 $R_f$=0.6

Analysis for the formula $C_{14}H_{17}ClN_4O_3S$ (356.9)

Calculated: Cl=9.94%, S=8.98%,

Found: Cl=9.82%, S=8.67%.

IR (KBr): $\nu$NH 3410, amide-I 1640, $NO_2$ 1530, 1370/cm

EXAMPLE 8

2-(N-Butylcarbamoylimino)-3=(5'=chloro-2'-nitrophenyl)-thiazolidine 1.3 g (5 mmoles) of 2-imino-3-(5-chloro-2'-nitrophenyl)-thiazolidine and 2.0 g (10 mmoles) of butyl isocyanate are boiled in 20 ml of acetonitrile for 10 hours. The solution is then clarified, evaporated in vacuo and the oily residue is crystallized from a slight amount of methanol.

Yield: 0.86 g (48%) of pale yellow crystalline powder

M.p.: 122–123° C. (MeOH)

TLC: Cyclohexane/ethyl acetate=1/2 $R_f$=0.5

Analysis for the formula $C_{13}H_{17}ClN_4O_3S$ (356.9)

Calculated: Cl=9.94%, S=8.98%,

Found: Cl=9.89%, S=9.28%.

IR (KBr): $\nu$NH 3430, amide-I 1650, $NO_2$ 1510, 1370/cm

EXAMPLE 9

2-(N-Propylcarbamoylimino)-3-(4'-chloro-2'-nitrophenyl)-thiazolidine 1.3 g (5 mmoles) of 2-imino-3-(4'-chloro-2'-nitrophenyl)-thiazolidine and 0.85 g (10 mmoles) of propyl isocyanate are boiled in 20 ml of acetonitrile for 6 hours. The solution is then clarified and evaporated in vacuo, the residue is crystallized from a slight amount of ethanol.

Yield: 1.1 g (64%) of pale yellow crystalline powder

M.p.: 150–151° C. (EtOH)

TLC: Cyclohexane/ethyl acetate=1/2 $R_f$=0.6

Analysis for the formula $C_{13}H_{15}ClN_4O_3S$ (342.9)

Calculated: Cl=10.35%, S=9.35%,

Found: Cl=10.56%, S=9.34%.

IR (KBr): $\nu$NH 3405, amide-I 1640, $NO_2$ 1530, 1370/cm

EXAMPLE 10

2-(N-Propylcarbamoylimino)-3-(5'-chloro-2'-nitrophenyl)-thiazolidine 1.3 g (5 mmoles) of 2-imino-3-(5'-chloro-2'-nitrophenyl)-thiazolidine and 0.85 g (10 mmoles) of propyl isocyanate are boiled in 20 ml of acetonitrile for 10 hours. The solution is then clarified and evaporated in vacuo, the residue is crystallized from a mixture of ethyl acetate and hexane.

Yield: 0.9 g (52%) of yellowish white crystalline powder

M.p.: 124-125° C. (EtOAc-hexane)

TLC: Cyclohexane/ethyl acetate=1/2 $R_f$=0.5

Analysis for the formula $C_{13}H_{15}ClN_4O_3S$ (342.9)

Calculated: Cl=10.35%, S=9.35%,

Found: Cl=10.20%, S=9.50%.

IR (KBr): $\nu$NH 3460, amide-I 1670, $NO_2$ 1530, 1370/cm

EXAMPLE 11

2-N'-(3-Dimethylaminopropyl-thiocarbamoyl)imino-3-(2'-nitrophenyl)-thiazolidine hydrochloride 1.1 g (5 mmoles) of 2-imino-3-(2'-nitrophenyl)-thiazolidine and 1.2 g (8 mmoles) of 3-dimethylaminopropyl isothiocyanate are boiled in 20 ml of acetonitrile for 8 hours. The solution is then clarified and evaporated in vacuo. The residual oil is stirred in methanol and saturated with gaseous hydrogen chloride for hour. The solution is evaporated in vacuo and the residue is crystallized from a mixture of ethanol and ether.

Yield: 2.0 g (98%) of yellow crystalline powder

M.p.: 173° C. (EtOH-ether)

TLC: MeOH $R_f$=0.3

Analysis for the formula $C_{15}H_{26}ClN_5O_2S_2$ (408)

Calculated: Cl=8.70%, N=17.17%, S=15.72%,

Found: Cl=8.86%, N=16.96%, S=15.75%.

IR (KBr): $\nu NO_2$ 1520, 1340, NH 3270, 1340/cm

EXAMPLE 12

2-(N'-Allylthiocarbamoylimino)-3-(2'-nitrophenyl)-thiazolidine 1.1 g (5 mmoles) of 2-imino-3-(2'-nitrophenyl)-thiazolidine and 0.75 g (7.5 mmoles) of allyl isothiocyanate are boiled in 20 ml of acetonitrile for 5 hours. The solution is then clarified and evaporated in vacuo and the residual yellow oil is crystallized from methanol.

Yield: 0.9 g (56%) of yellow crystalline powder

M.p.: 102-103° C. (MeOH)

TLC: Cyclohexane/ethyl acetate=1/2 $R_f$=0.8

Calculated: N=17.38%, S=19.88%,

Found N=17.21%, S=20.17%.

IR (KBr): $\nu$NH 3460, $NO_2$ 1530, 1370,=$CH_2$ 1630, 950/cm

EXAMPLE 13

2-(N'-Allylthiocarbamoylimino)-3-(5'-methoxy-2-nitrophenyl)-thiazolidine 1.7 g (5 mmoles) of 2-imino-3-(5'-methoxy-2'-nitrophenyl)-thiazolidine hydrobromide are suspended in 20 ml of ethanol under stirring. The base is liberated with diazomethane. The solution is evaporated in vacuo, the residue is dissolved in 20 ml of acetonitrile, 0.75 ml of allyl isothiocyanate are added to it and the mixture is boiled for 4 hours. After clarification the solution is evaporated in vacuo and the residual yellow oil is crystallized from n-propanol.

Yield: 1.1 g (62%) of yellow crystalline powder

M.p.: 114-115° C. (n-PrOH)

TLC: Cyclohexane/ethyl acetate=3/2 $R_f$=0.4

Analysis for the formula $C_{14}H_{16}N_4O_3S_2$ (352.4)

Calculated: N=15.90%, S=18.20%,

Found: N=16.15%, S=18.03%,

IR (KBr): NH 3370, $NO_2$ 1520, 1350=$CH_2$ 1620, 910/cm

EXAMPLE 14

2-(N'-Allylthiocarbamoylimino)-3-(4'-chloro-2'-nitrophenyl)-thiazolidine 1.3 g (5 mmoles) of 2-imino-3-(4'-chloro-2'-nitrophenyl)-thiazolidine and 0.75 g (7.5 g (7.5 mmoles) of allyl isothiocyanate are boiled in 30 ml of acetonitrile for 5 hours. The solution is then clarified and evaporated in vacuo. The solid residue is crystallized from methanol.

Yield: 1. 1 g (61%) of yellow crystalline powder

M.p.: 111-113° C. (MeOH)

TLC: Cyclohexane/ethyl acetate=3/2, $R_f$=0.5

Analysis for the formula $C_{13}H_{13}ClN_4O_2S_2$ (356.9)

Calculated: Cl=3.94%, N=15.70%, S=17.96%,

Found: Cl=10.26%, N=15.40%, S=18.20%.

IR (KBr): $\nu$3380, $NO_2$ 1540, 1370=$CH_2$ 1630, 950/cm

EXAMPLE 15

2-N'-[3-Dimethylaminopropyl)-thiocarbamoylimino]-3-(4'-chloro-2'-nitrophenyl)-thiazolidine hydrochloride 2.6 g (10 mmoles) of 2-imino-3-(4'-chloro-2'-nitrophenyl-thiazolidine and 2.3 g (16 mmoles) of 3-dimethylaminopropyl isothiocyanate are boiled in 50 ml of acetonitrile for 14 hours. The solution is then clarified and evaporated and the residual yellow oil is boiled for 1 hour in 20 ml of methanol saturated with gaseous hydrogen chloride. The solution is evaporated in vacuo and the solid residue is crystallized from isopropanol.

Yield: 3.9 g (89%)

M.p.: 207-208° C. (i-PrOH)

TLC: Benzene/methanol=1/3 $R_f$=0.4

Analysis for the formula $C_{15}H_{21}Cl_2N_5O_2S$

Calculated: Cl=16.15%, S=14.62%,

Found: Cl=15.98%, S=15.05%.

IR (KBr): $\nu NO_2$ 1530, 1350, NH 3260, 2620/cm

EXAMPLE 16

2-N'-[3-Dimethylaminopropyl)-thiocarbamoylimino]-3-(5-chloro-2'-nitrophenyl)-thiazolidine 1.8 g (7 mmoles) of 2-imino-3-(5'-chloro-2'-nitrophenyl)-thiazolidine and 1.6 g (11 mmoles) of 3-dimethylaminopropyl isothiocyanate are boiled in 30 ml of acetonitrile for 12 hours. The solution is then clarified, evaporated and the residual oil is crystallized from 20 ml of ethanol.

Yield: 2.0 g (71%) of yellow crystalline powder

M.p.: 135-136° C. (EtOH)

TLC: Cyclohexane/ethyl acetate=3/2 $R_f$=0.4

Analysis for the formula $C_{15}H_{20}ClN_5O_2S_2$ (402.0)

Calculated: Cl=8.83%, S=15.96%,

Found: Cl=8.85%, S=16.46%.

IR (KBr): $\nu NO_2$ 1530, 1350, NH 3450, 3100/cm

EXAMPLE 17

2=(N'-Allylthiocarbamoylimino)=3=(2'-nitro-4'-trifluoromethyl-phenyl)-thiazolidine 2.9 g (10 mmoles) of 2-imino-3-(2'-nitro-4'-trifluromethyl-phenyl)-thiazolidine and 2 ml (2 g, 20 mmoles) of allyl isothiocyanate are boiled in 30 ml of acetonitrile for 4 hours. The solution is evaporated in vacuo and the residue is triturated with hexane.

Yield: 2.3 g (59%) of pale yellow crystalline powder

M.p.: 140-141° C. (MeOH)

Analysis for the formula $C_{14}H_{13}F_3N_4O_2S_2$ (390.4)

Calculated: N=14.35%, S=16.42%,

Found: N=14.35%, S=16.69%.
IR (KBr): νNH 3370, C(=S)N 1490/cm δ=CH₂ 910, 830/cm

EXAMPLE 18

2-(N'-Methylcarbamoylimino)-3-(5'-chloro-2'-nitrophenyl)-thiazolidine 2.6 g (10 mmoles) of 2imino-3-(5'-chloro-2'-nitrophenyl)-thiazolidine and 1.8 g (25 m methyl isothiocyanate are boiled in 30 ml of acetonitrile for 5 hours. The solution is then clarified, filtered, evaporated in vacuo and the residual oil is crystallized from isopropanol.

Yield: 2.2 g (66.5%) of yellowish white crystalline powder

M.p.: 158–159° C. (i-PrOH)
Analysis for the formula $C_{11}H_{11}ClN_4O_2S_2$ (330.9)
Calculated: Cl=10.72%, S=16.99%,
Found: Cl=10.63%, S=16.96%,
IR (KBr): NH 3220; C(=S)N 1490/cm
¹H-NMR: δ3.05 d(3H); 3.35 m(2H); 4.05 m(2H); (COCl₃) 6.5 s(NH); 7.2–8.0 m (3H)

EXAMPLE 19

2-[(N-Methylcarbamoyl)-imino]-3-(5-chloro-2-nitrophenyl)-thiazolidine 2.6 g (10 mmoles) of 2-imino-3-(5-chloro-2-nitrophenyl)-thiazolidine and 1.14 g of methyl isocyanate are boiled in 30 ml of acetonitrile for 2 hours. The mixture is then cooled, the separated crystals are filtered and washed with hexane.

Yield: 2.7 g (66%) of yellowish white crystalline powder

M.p.: 218–220° C. (i-PrOH)
TLC: Chloroform/ethyl acetate=1/2 $R_f$=0.5
Analysis for the formula $C_{11}H_{11}ClN_4O_3S$ (314.8)
Calculated: Cl=11.27%, S=10.18%,
Found: Cl=11.09%, S=10.30%,
IR (KBr): νNH 3200, amide-I 1620, NO₂ 1510, 1340/cm

EXAMPLE 20

2-(N'-Allylthiocarbamoylimino)-3-(5'-chloro-2'-nitrophenyl)-thiazolidine 2.6 g (10 mmoles) of 2-imino-3-(5'-chloro-2'-nitrophenyl)-thiazolidine and 1.5 ml (1.5 g, 15 mmoles) of allyl isothiocyanate are boiled in 40 ml of acetonitrile for 4 hours. The solution is evaporated in vacuo and the residual oil is crystallized by triturating it with a slight amount of ether.

Yield: 2.4 g (67%) of yellowish white crystalline powder

M.p.: 156–158° C. (i-PrOH)
Analysis for the formula $C_{13}H_{13}ClN_4O_2S_2$ (356.9)
Calculated: Cl=9.94%, S=17.96%,
Found Cl=10.07%, S=18.20%,
IR (KBr): νNH 3300; C(=S)N 1490/cm

EXAMPLE 21

2-(N'-Methylthiocarbamoylimino)-3-(2'-nitro-4'-trifluoromethyl-phenyl)-thiazolidine 2.9 g (10 mmoles) of 2-imino-3-(2'-nitro-4'-trifluoromethyl-phenyl)-thiazolidine and 1.2 g (16.5 mmoles) of methyl isothiocyanate are boiled in ml of acetonitrile for 4 hours. The solution is evaporated in vacuo and the crystalline residue is crystallized from methanol.

Yield: 1.8 g (53%) of yellowish white crystalline powder

M p.: 169–171° C. (MeOH)
Analysis for the formula $C_{12}H_{11}F_3N_4S_2O_2$ (340.4)
Calculated: N=16 48%, S=18.84%,
Found: N=16.18%, S=18.38%.
IR (KBr): νNH 3170; C(=S)N 1500; C=S 1140/cm
$^L$H-NMR(CDCl₃) 3.1 d(3H); 3.3 t (2H); 4.1 t (2H); 6.6 s (NH); 7.25-8.1 m (3H)

EXAMPLE 22

2-[(N-3-Chlorophenylcarbamoyl)-imino]-3-(2-nitro-4-trifluoromethyl-phenyl)-thiazolidine 2.9 g (10 mmoles) of 2-imino-3-(2-nitro-4-trifluoromethyl-phenyl)-thiazolidine and 1.85 g (12 mmoles) of 3-chlorophenyl isocyanate are boiled in 30 ml of acetonitrile for 1 hour. The mixture is then cooled and the separated crystals are washed with ether.

Yield: 3.1 g (70%) of pale yellowish white crystalline powder

M.p.: 198–200° C. (i-PrOH)
TLC: Cyclohexane/ethyl acetate=1/2 $R_f$=0.6
Analysis for the formula $C_{17}H_{12}ClF_3N_4O_3S$ (444.8)
Calculated: N=12.60%, S=7.20%,
Found: N=12.59%, S=7.65%.
IR (KBr): νNH 3210, amide-I 1630, NO₂ 1510, 1340/cm

EXAMPLE 23

2-[(N-Phenylthiocarbamoyl)-imino]-3-(2-nitro-4-trifluoromethyl-phenyl)-thiazolidine 2.9 g (10 mmoles) of 2-imino-3-(2-nitro-4-trifluoromethyl-phenyl)-thiazolidine and 1.3 ml (1.5 g, 11 mmoles) of phenyl isothiocyanate are boiled in 30 ml of acetonitrile for 4 hours. The mixture is then cooled, the separated crystals are filtered and washed with pentane.

Yield: 3.5 g (89%) of pale yellowish white crystalline powder

M.p.: 168–169° C. (i-PrOH)
TLC: Cyclohexane/ethyl acetate=3/2 $R_f$=0.7
Analysis for the formula $C_{17}H_{13}F_3N_4O_2S_2$ (394.4)
Calculated: N=13.14%, S=15.04%,
Found: N=13.04%, S=15.36%,
IR (KBr): νNH 3160, NO₂ 1510, 1320/cm

EXAMPLE 24

2-Acetylimino-3-(4'-chloro-2'-nitrophenyl)-thiazolidine a) 2.6 g (10 mmoles) of 2-imino-3-(4'-chloro-2'-nitrophenyl)-thiazolidine are boiled in a mixture of 5 ml of acetic acid and 5 ml of acetic anhydride for half an hour. The solution is then poured onto 30 ml of icy water and extracted three times with 20 ml of dichloromethane each. The organic phases are combined and washed three times with 20 ml of 5% aqueous sodium carbonate solution each and with water. The solution is then dried and evaporated. The oily residue is crystallized from ethyl acetate.

Yield: 2.3 g (77%) of yellowish white needle crystals
M.p : 127–128° C. (EtOAc)
TLC: Cyclohexane/ethyl acetate=3/2 $R_f$=0.3
Analysis for the formula $C_{11}H_{10}ClN_3O_3S$ (299.7)
Calculated: Cl=11.84%, N=14.02%, S=10.70%,
Found: Cl=11.64%, N=13.80%, S=10.69%.
IR (KBr): vamide-I 1630, NO₂ 1520, 1350/cm b) 0.52 g (2 mmoles) of 2-imino-3-(4'-chloro-2-nitrophenyl)-thiazolidine is dissolved in 20 ml of anhydrous chloroform. 0.24 g (0.21 ml, 3 mmoles) of acetyl chloride and 0.4 ml (0.3 g, 3 mmoles) of triethylamine are added to the solution and it is boiled for 30 minutes. The solution is then evaporated in vacuo, the oily residue is dissolved in 30 ml of dichloromethane and extracted twice with 10 ml of saturated aqueous sodium chloride solution each. The solution is dried and evaporated, the oily residue is crystallized from ethyl acetate.

Yield: 0.4 g (67%)
M.p.: 127–128° C.

According to IR and TLC analyses the product thus obtained is identical to the compound prepared according to variant a).

EXAMPLE 25

L-Acetylimino=3-(2-nitrophenyl)-thiazolidine 7.5 g (33.6 mmoles) of 2-imino-3-(2-nitrophenyl)-thiazolidine are boiled in a mixture of 15 ml of acetic anhydride and 20 ml of acetic acid, in the presence of 0.2 g of zinc powder for 30 minutes. The mixture is then evaporated in vacuo, the crystalline residue is dissolved in 50 ml of hot ethyl acetate and filtered while it is still hot. Then it is cooled and the separated crystals are filtered while they are still hot and washed twice with 10 ml of ether each.

Yield: 6.8 g (76.3%)
M.p. 173–174° C. (EtOAc)
Analysis for the formula $C_{11}H_{11}N_3O_3S$ (265.3)
Calculated: N=15.83%, S=12.08%,
Found: N=15.47%, S=12.58%.

EXAMPLE 26

2-Acetylimino-3-(4'-trifluoromethyl-2'-nitrophenyl)-thiazolidine 2.9 g (10 mmoles) of 2-imino-3-(4'-trifluoromethyl-2'-nitrophenyl)-thiazolidine are boiled in a mixture of 5 ml of acetic acid and 5 ml of acetic anhydride for 1 hour. The solution is then poured onto 30 ml of icy water, the separated crystals are filtered and washed with water.

Yield: 2.9 g (87%) of yellowish white crystalline powder
M.p.: 144–145° C. (EtOAc-hexane)
TLC: Cyclohexane/ethyl acetate=1/2 $R_f$=0.5
Analysis for the formula $C_{12}H_{10}F_3N_3O_3S$ (333.3)
Calculated: N=12 60%, S=9.62%,
Found: N=12.39%, S=9.45%.
IR (KBr): amide-I 1620, $NO_2$ 1520, 1340/cm

EXAMPLE 27

2-Formylimino-3-(4'-chloro-2'-nitrophenyl)-thiazolidine 0.52 g (2 mmoles) of 2-imino-3-(4'-chloro-2-nitrophenyl)-thiazolidine and 0.9 g (10 mmoles) of acetic acid-formic acid mixed anhydride are boiled in 10 ml of anhydrous chloroform for 30 minutes. The solution is then evaporated in vacuo and the oily residue is crystallized from methanol.

Yield: 0.45 g (79%) of yellowish white crystalline powder
M.p.: 128–129° C. (MeOH)
TLC: Cyclohexane/ethyl acetate=3/2 $R_f$=0.3
Analysis for the formula $C_{10}H_8ClN_3O_3S$ (235.8)
Calculated: Cl=12.42%, S=11.22%,
Found: Cl=12 67%, S=11.38%.
IR (KBr): $\nu$CH 2900, amide-I 1634, $NO_2$ 1530, 1355/cm

EXAMPLE 28

2-[(N-Allylthiocarbamoyl)-imino]-3-(2'-chloro-6'-nitrophenyl)-thiazolidine 1.04 g (4 mmoles) of 2-imino-3-(2'-chloro-6'-nitrophenyl)-thiazolidine and 0.8 ml (0.81 g, 8 mmoles) of allyl isothiocyanate are boiled in 20 ml of acetonitrile for 5 hours. The solution is then clarified and evaporated in vacuo. The residual yellow oil is crystallized from methanol.

Yield: 0.8 g (56%) of yellowish white crystalline powder
M.p.: 110–112° C. (MeOH)
Analysis for the formula $C_{13}H_{13}ClN_4O_2S_2$ (356.9)
Calculated: Cl=9.95%, S=17.97%,
Found: Cl=9.99%, S=17.49%.
IR (KBr): $\nu$NH 3280, $NO_2$ 1520, 1340/cm

EXAMPLE 29

3-(2'-Chloro-6'-nitrophenyl)-2-[N-propylcarbamoyl)-imino]-thiazolidine 0.93 g (3.6 mmoles) of 2-imino-3-(2'-chloro-6'-nitrophenyl)-thiazolidine and 0.6 ml (0.5 g, 6 mmoles) of propyl isocyanate are boiled in 20 ml of acetonitrile for 3 hours. The solution is then clarified and evaporated in vacuo. The crystalline residue is recrystallized from a mixture of ethyl acetate and hexane.

Yield: 0.9 g (72.9%) of yellowish white crystalline powder
M.p.: 132–134° C. (EtOAc-hexane)
TLC: Cyclohexane/ethyl acetate=1/2 $R_f$=0.6
Analysis for the formula $C_{13}H_{15}ClN_4O_3S$ (342.9)
Calculated: Cl=10.35%, S=9.35%,
Found: Cl=10.41%, S=9.01%,
IR (KBr): $\nu$NH 3420, amide-I 1620, $NO_2$ 1520, 1350/cm

EXAMPLE 30

3-(3'-Chloro-2'-nitrophenyl)-2-[N-propylcarbamoyl)-imino]-thiazolidine 0.31 g (1.2 mmoles) of 2-imino-3-(3'-chloro-2'-nitrophenyl)-thiazolidine and 0.2 ml (0.17 g, 2 mmoles) of propyl isocyanate are boiled in 15 ml of acetonitrile for 1.5 hours. The solution is then clarified and evaporated in vacuo. The residual oil gets crystalline upon triturating with ether.

Yield: 0.24 g (58%)
M.p.: 94° C. (EtOAc-hexane)
TLC: Benzene/acetone=1/1 $R_f$=0.8
Analysis for the formula $C_{13}H_{15}ClN_4O_3S$ (342.9)
Calculated: Cl=10.35%, S=9.35%,
Found: Cl=10.64%, S=9.51%,
IR (KBr): $\nu$NH 3380, amide-I 1620, $NO_2$ 1530, 1355/cm

EXAMPLE 31

2-[(N-Allylthiocarbamoyl)-imino]-3-(2'-chloro-4'-nitrophenyl)-thiazolidine 1.52 g (2 mmoles) of 2-imino-3-(2'-chloro-4'-nitrophenyl)-thiazolidine and 0.4 ml (0.4 g, 4 mmoles) of allyl isothiocyanate are boiled in 15 ml of acetonitrile for 6 hours. The solution is then clarified and evaporated in vacuo. The crystalline residue is recrystallized from methanol.

Yield: 0.6 g (84%) of yellowish white crystalline powder
M.p.: 154–155° C. (MeOH)
Analysis for the formula $C_{13}H_{13}ClN_4O_2S_2$ (356.9)
Calculated: Cl=9.95%m S=17.97%,
Found: Cl=9.48%, S=17.82%.
IR (KBr): $\nu$NH 3260, $NO_2$ 1525, 1350/cm

EXAMPLE 32

3-(2'-Chloro-4'-nitrophenyl)-2-[N-propyl-carbamoyl)-imino]-thiazolidine 0.31 g (1.2 mmoles) of 2-imino-3-(2'-chloro-4'-nitrophenyl)-thiazolidine and 0.2 ml (0.17 g, 2 mmoles) of propyl isocyanate are boiled in 15 ml of acetonitrile for 2.5 hours. The solution is then evaporated in vacuo and the oily residue is crystallized from a mixture of ethyl acetate and hexane.

Yield: 0.3 g (73%) of yellowish white crystalline powder

M.p.: 148° C. (ethyl acetate-hexane)
TLC: Benzene/acetone=1/1 $R_f$=0.8
Analysis for the formula $C_{13}H_{15}ClN_4O_3S$ (342.9)
Calculated: Cl=10.35%, S=9.35%,
Found: Cl=10.38%, S=9.20%,
IR (KBr): $\nu$NH 3470, amide-I 1650, $NO_2$ 1510, 1340/cm

EXAMPLE 33

(R,S)-3-(4'-Chloro-2'-nitrophenyl)-5-methyl-2-[(N-propylcarbamoyl)-imino]-thiazolidine 2.7 g (10 mmoles) of (R,S)-2-imino-3-(4'-chloro-2'-nitrophenyl)-5-methylthiazolidine and 2 ml (1.7 g, 19 mmoles) of propyl isocyanate are boiled in 20 ml of acetonitrile for 4 hours. The solution is then evaporated in vacuo and the crystalline residue is recrystallized from ethyl acetate.

Yield: 3.1 g (87%) of pale yellow crystalline powder
M.p.: 168–170° C. (EtOAc)
TLC: Benzene/acetone=1/1 $R_f$=0.8
Analysis for the formula $C_{14}H_{17}ClN_4O_3S$ (356.9)
Calculated: Cl=9.94%, S=8.98%,
Found: Cl=9.95%, S=9.07%.
IR (KBr): NH 3460, amide-I 1640, $NO_2$ 1530, 1350/cm

EXAMPLE 34

(R,S)-2-[(N-Allylthiocarbamoyl)-imino]-4-ethyl-3-(4'-chloro-2'-nitrophenyl)-thiazolidine 0.57 g (2 mmoles) of (R,S)-4-ethyl-2-imino-3-(4'-chloro-2'-nitrophenyl)-thiazolidine and 0.4 (0.4 g, 4 mmoles) of allyl isothiocyanate are boiled in 10 ml of acetonitrile for 6 hours. The solution is then evaporated in vacuo. The residual yellow oil gets crystalline upon triturating with hexane.

Yield: 0.69 g (89%) of pale yellow crystalline powder
M.p.: 140° C. (MeOH)
TLC: Cyclohexane/ethyl acetate=1/2 $R_f$=0.8
Analysis for the formula $C_{15}H_{17}ClN_4O_2S_2$ (384.9)
Calculated: Cl=9.22%, S=16.66%,
Found: Cl=9.42%, S=16.55%,
IR (KBr): $\nu$NH 3240, $NO_2$ 1530, 1350/cm

EXAMPLE 35

(R,S)-2-[(N-Allylthiocarbamoyl)-imino]-3-(4'-chloro-2'-nitrophenyl)-5-methyl-thiazolidine 1.36 g (5 mmoles) of (R,S)-2-imino-3-(4'-chloro-2'-nitrophenyl)-5-methyl-thiazolidine and 1 ml (1.02 g, 10 mmoles) of allyl isothiocyanate are boiled in 15 ml of acetonitrile for 3 hours. The solution is then evaporated in vacuo. The residual yellow oil gets crystalline upon triturating with hexane.

Yield: 1.1 g (59.5%) of pale yellow crystalline powder
M.p.: 110° C. (MeOH)
TLC: Cyclohexane/ethyl acetate=1/2 $R_f$=0.6
Analysis for the formula $C_{14}H_{15}ClN_4S_2O_2$ (370.9)
Calculated: Cl=9.57%, S=17.29%,
Found: Cl=9.54%, S=17.31%,
IR (KBr): NH 3410, $NO_2$ 1530, 1360/cm

EXAMPLE 36

2-[(N-Ethylcarbamoyl)-imino]-3-(5'-chloro-2'-nitrophenyl)-thiazolidine 1.3 g (5 mmoles) of 2-imino-3-(4'-chloro-2-nitrophenyl)-thiazolidine and 1 g (14 mmoles) ethyl isocyanate are boiled in 30 ml of acetonitrile for 3 hours. The solution is then clarified, evaporated in vacuo and the crystalline residue is recrystallized from methanol.

Yield: 0.85 g (52%) of yellowish white crystalline powder

M.p.: 162–164° C. (MeOH)
TLC: Cyclohexane/ethyl acetate=1/2 $R_f$=0.6
Analysis for the formula $C_{12}H_{13}ClN_4O_3S$ (328.8)
Calculated: Cl=10.79%, S=9.75%,
Found: Cl=10.61%, S=9.72%.
IR (KBr): $\nu$NH 3370, amide-I 1620, $NO_2$ 1515, 1345/cm

EXAMPLE 37

3-(5'-Chloro-2'-nitrophenyl)-2-[(N-isopropyl-carbamoyl)-imino]-thiazolidine 1.3 g (5 mmoles) of 2-imino-3-(5'-chloro-2'-nitrophenyl)-thiazolidine and 1 g (12 mmoles) of isopropyl cyanate are boiled in 30 ml of acetonitrile for 2 hours. The solution is then clarified and evaporated in vacuo. The residual oil is crystallized from a mixture of ethyl acetate and hexane.

Yield: 0.9 g (53%) of pale yellow crystalline powder
M.p.: 145–146° C. (EtOAc-hexane)
TLC: Cyclohexane/ethyl acetate=1/2 $R_f$=0.6
Analysis for the formula $C_{13}H_{15}ClN_4O_3S$ (342.8)
Calculated: Cl=10.34%, S=9.36%,
Found: Cl=10.03%, S=9.51%.
IR (KBr): $\nu$NH 3450, amide-I 1640, $NO_2$ 1520, 1360/cm

EXAMPLE 38

2-[(N-Ethylcarbamoyl)-imino]-3-(4'-chloro-2'-nitrophenyl)-thiazolidine 1.3 g (5 mmoles) of 2-imino-3-(4'-chloro-2-nitrophenyl)-thiazolidine and 1 g (14 mmoles) ethyl isocyanate are boiled in 30 ml of acetonitrile for 4 hours. The solution is then clarified, evaporated in vacuo and the crystalline residue is recrystallized from methanol.

Yield: 0.9 g (55%) of yellowish white crystalline powder

M.p.: 174–175° C. (MeOH)
TLC: Cyclohexane/ethyl acetate=1/2 $R_f$=0.7
Analysis for the formula $C_{12}H_{13}ClN_4O_3S$ (328.8)
Calculated: Cl=10.79%, S=9.75%,
Found: Cl=10.88%, S=9.89%.
IE (KBr): $\nu$NH 3350, amide-I 1625, $NO_2$ 1535, 1365/cm

EXAMPLE 39

3-(4'-Chloro-2'-nitrophenyl)-2-[(N-isopropylcarbamoyl)-imino]-thiazolidine 1.3 g (5 mmoles) of 2-imino-3-(4'-chloro-2'-nitrophenyl)-thiazolidine and 1 g (12 mmoles) of isopropyl cyanate are boiled in 30 ml of acetonitrile for 3 hours. The solution is then clarified, evaporated in vacuo and the crystalline residue is recrystallized from methanol.

Yield: 1.2 g (70%) of yellowish white crystalline powder

M.p.: 158–159° C. (MeOH)

TLC: Cyclohexane/ethyl acetate = 1/2 $R_f$=0.6

Analysis for the formula $C_{13}H_{15}ClN_4O_3S$ (342.8)

Calculated: Cl=10.34%, S=9.36%,

Found: Cl=10.40%, S=9.38%.

IR (KBr): NH 3210, amide-I 1645, $NO_2$ 1530, 1360/cm

EXAMPLE 40

2-[(N-Ethylthiocarbamoyl)-imino]-3-(4'-chloro-2'-nitrophenyl)-thiazolidine 1.3 g (5 mmoles) of 2-imino-3-(4'-chloro-2'-nitrophenyl)-thiazolidine and 1.65 g (20 mmoles) of ethyl isocyanate are boiled in 30 ml of acetonitrile for 8 hours. The solution is then clarified, evaporated in vacuo and the crystalline residue is recrystallized from acetonitrile.

Yield: 0.95 g (55%) of pale yellow crystalline powder

M.p.: 170–171° C. (MeOH)

TLC: Cyclohexane/ethyl acetate = 1/2 $R_f$=0.8

Analysis for the formula $C_{12}H_{13}ClN_4O_2S_2$ (344.8)

Calculated: Cl=10.29%, S=18.39%,

Found: Cl=10.15%, S=18.39%.

IR (KBr): $\nu$NH 3380, $NO_2$ 1530, 1365/cm

EXAMPLE 41

2-[(N-Butylthiocarbamoyl)-imino]-3-(4'-chloro-2'-nitrophenyl)-thiazolidine 1.3 g (5 mmoles) of 2-imino-3-(4'-chloro-2'-nitrophenyl)-thiazolidine and 1.7 g (15 mmoles) of butyl isothiocyanate are boiled in 30 ml of acetonitrile for 10 hours. The solution is then clarified and evaporated in vacuo. The yellowish green oily residue is crystallized from methanol.

Yield: 1.2 g (66%) of yellowish white crystalline powder

M.p. 130° C. (MeOH)

TLC: Cyclohexane/ethyl acetate = 1/2 $R_f$=0.8

Analysis for the formula $C_{14}H_{17}ClN_4O_2S_2$ (372.9)

Calculated: Cl=9.52%, S=17.19%,

Found: Cl=9.93%, S=16.88%,

IR (KBr): $\nu$NH 3380, $NO_2$ 1530, 1355/cm

EXAMPLE 42

2-[(N-tert-Butylthiocarbamoyl)-imino]-3-(4'-chloro-2'-nitrophenyl)-thiazolidine 1.3 g (5 mmoles) of 2'-nitrophenyl)-thiazolidine and 17 g (15 mmoles) of tert-butyl isothiocyanate are boiled in 30 ml of acetonitrile for 12 hours. The solution is then clarified and evaporated. The yellow crystalline residue is recrystallized from ethanol.

Yield: 0.7 g (38%) of yellowish white crystalline powder

M.p.: 168–170° C. (EtOH)

TLC: Cyclohexane/ethyl acetate = 3/2 $R_f$=0.8

Analysis for the formula $C_{14}H_{17}ClN_4O_2S_2$ (372.9)

Calculated: Cl=9.52%, S=17.19%,

Found: Cl=9.38%, S=17.49%.

IR (KBr): $\nu$NH 3220, $NO_2$ 1530, 1350/cm

EXAMPLE 43

2-[(N-tert-Butylthiocarbamoyl)-imino]-3-(5'-chloro-2'-nitrophenyl)-thiazolidine 1.3 g (5 mmoles) of 2-imino-3-(5'-chloro-2'-nitrophenyl)-thiazolidine and 1.7 g (15 mmoles) of tert-butyl isothiocyanate are boiled in 30 ml of acetonitrile for 15 hours. The solution is then clarified and evaporated, then the yellow crystal-line residue is recrystallized from ethanol.

Yield: 0.9 g (48%) of yellowish white crystalline powder

M.p.: 181–182° C. (MeOH)

TLC: Cyclohexane/ethyl acetate = 3/2 $R_f$=0.6

Analysis for the formula $C_{14}H_{17}ClN_4O_2S_2$ (372.9)

Calculated: Cl=9.52%, S=17.19%,

Found: Cl=9.74%, S=17.23%.

IR (KBr): $\nu$NH 3330, $NO_2$ 1525, 1350/cm

EXAMPLE 44

2-[(N-Ethyl-S-methyl-isothiocarbamoyl)imino]-3-(5'-chloro-2'-nitrophenyl)-thiazol hydroiodide 1.7 g (5 mmoles) of 2-[(N-ethylthiocarbamoyl)-imino]-3-(5'-chloro-2'-nitrophenyl)-thiazolidine and 1.5 ml (3.4 g, 25 mmoles) of methyl iodide are boiled in 20 ml of anhydrous methanol for 1.5 hours. The solution is then clarified and evaporated in vacuo, then the crystalline residue is recrystallized from ethanol.

Yield: 1 8 g (74%) of yellow crystalline powder

M.p.: 194–196° C.

TLC: Cyclohexane/ethyl acetate = 3/2 $R_f$=0.5

Analysis for the formula $C_{13}H_{16}ClN_4O_2S_2$ (486.8)

Calculated: N=11.51%, S=13.17%,

Found: N=11.52%, S=13.60%,

IR (KBr): $\nu NO_2$ 1530, 1350/cm

EXAMPLE 45

2-[(N'-Allyl-s-methyl-isothiocarbamoyl)imino]-3-(5'-chloro-2'-nitrophenyl)-thiazolidine hydroiodide 1.8 g (5 mmoles) of 2-(N-allylthiocarbamoylimino)-3-(5'-chloro-2'-nitrophenyl)-thiazolidine and 1.5 ml (3.4 g, 25 mmoles) of methyl iodide are boiled in 40 ml of anhydrous methanol for 1.5 hours. The solution is then clarified and filtered, then evaporated and cooled. The separated crystals are filtered and washed with ether.

Yield: 2.2 g (88%) of yellow crystalline powder

M.p. 184° C. (n-PrOH)

TLC: Cyclohexane/ethyl acetate = 3/2 $R_f$=0.6

Analysis for the formula $C_{14}H_{16}ClN_4O_2S_2$ (498.8)

Calculated: N=11.23%, S=12.85%,

Found: N=11.20%, S=13.28%.

IR (KBr): $\nu NO_2$ 1530, 1350, =$CH_2$, 920/cm

EXAMPLE 46

2-Cyanimido-3-(5'-chloro-2'-nitrophenyl)thiazolidine 2.6 g 10 mmoles) of 2-imino-3-(5'-chloro-2'-nitrophenyl)-thiazolidine and 1.5 g (14 mmoles) of bromine cyan are boiled in 50 ml of acetonitrile for 3 hours. While boiling crystals begin to separate. The mixture is cooled, then the separated crystals are filtered and washed with ether.

Yield: 2.6 g (92%) of yellowish white crystalline powder

M.p.: 202° C. (acetonitrile)

Analysis for the formula $C_{10}H_7ClN_4O_2S$ (282.8)

Calculated: Cl=12.55%, S=11.34%,

Found: Cl=12.38%, S=11.83%.

EXAMPLE 47

2-Cyanimido-3-(2'-nitro-4'-trifluormethylphenyl)-thiazolidine hydrobromide 2.9 g (10 mmoles) of 2-imino-3-(2'-nitro-4'-trifluromethyl-phenyl)-thiazolidine and 1.5 g (14 mmoles) of bromine cyan are boiled in 50 ml of acetonitrile for 3 hours. The solution is cooled, then the separated crystals are filtered and washed with ether.

Yield: 2.8 g (71%) of yellowish white crystalline powder

M.p.: 263–264° C, (glacial acid-ether)

Analysis for the formula $C_{11}H_8BrF_3N_4O_2S$ (397.2)

Calculated: Br=20.13%, S=8.07%,

Found: Br=20.05%, S=8.14%.

IR (KBr): C=N inactive $^1$H-NMR DMSO-d6 3.7 t (2H); 4.3 t (2H) 7.7–8.4 m (3H) 9.8 s (NH)

What we claim is:

1. A compound selected from the group consisting of 2-(N'-allylthiocarbamoylimino)-3-(5'-chloro-2'-nitrophenyl)-thiazolidine, 2-cyanimido-3-(5'-chloro-2'-nitrophenyl)-thiazolidine, 2-acetylimino-3-(4'-chloro-2'-nitrophenyl)-thiazolidine, and pharmaceutically acceptable salts thereof.

2. Method of antianginal and/or analgesic treatment, which comprises administering to a patient an effective amount of a compound of the formula (I)

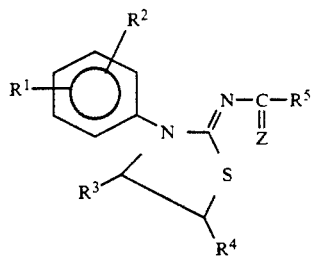

wherein
$R^1$ and $R^2$ each represent halogen, nitro, $C_{1-4}$ alkoxy or $C_{1-4}$ alkyl, which latter may optionally carry one or more halogen substituent(s), $R^3$ and $R^4$ each represent hydrogen or $C_{1-4}$ alkyl, Z denotes oxygen, sulfur or imino, which latter is substituted by a $C_{1-6}$ alkyl or a $C_{1-6}$ alkenyl group, $R^5$ stands for hydrogen, $C_{1-4}$ alkyl, $C_{1-4}$ alkylthio or a group of the formula —NH—R, wherein R represents $C_{1-6}$ alkyl, aryl, aralkyl or $C_{1-6}$ alkenyl optionally carrying a halogen or a di-($C_{1-4}$ alkyl)-amino substituent; or Z and $R^5$ together stand for a trivalent nitrogen atom, with the proviso that if Z denotes a substituted imino group, then $R^5$ stands for $C_{1-4}$ alkylthio, and if $R^5$ is $C_{1-4}$ alkylthio, then Z represents a substituted imino, and with the further proviso that if Z denotes sulfur, $R^5$ is other than hydrogen or $C_{1-4}$ alkyl, or a pharmaceutically acceptable salt thereof.

* * * * *